US008642304B2

(12) United States Patent
Raap et al.

(10) Patent No.: US 8,642,304 B2
(45) Date of Patent: Feb. 4, 2014

(54) PROCESS FOR PRODUCING METHANE FROM BIOMASS

(75) Inventors: Johannes Franciscus Maria Raap, 's-Hertogenbosch (NL); Petrus Wilhelmus Alphonsus Maria Brooijmans, Dongen (NL)

(73) Assignee: Koninklijke Cooperatie Cosun U.A., Breda (NL)

( * ) Notice: Subject to any disclaimer, the term of this patent is extended or adjusted under 35 U.S.C. 154(b) by 0 days.

(21) Appl. No.: 13/264,708

(22) PCT Filed: Apr. 15, 2010

(86) PCT No.: PCT/NL2010/050193
§ 371 (c)(1),
(2), (4) Date: Dec. 21, 2011

(87) PCT Pub. No.: WO2010/120173
PCT Pub. Date: Oct. 21, 2010

(65) Prior Publication Data
US 2012/0094350 A1    Apr. 19, 2012

(30) Foreign Application Priority Data

Apr. 17, 2009   (EP) .................................... 09158176

(51) Int. Cl.
*C12P 5/02*         (2006.01)
(52) U.S. Cl.
USPC ....................................................... 435/167
(58) Field of Classification Search
None
See application file for complete search history.

(56) References Cited

U.S. PATENT DOCUMENTS

| 4,022,665 | A | 5/1977 | Ghosh et al. | |
| 5,057,284 | A | 10/1991 | Emmett, Jr. et al. | |
| 6,551,510 | B1 * | 4/2003 | Bakke et al. | 210/603 |
| 7,276,148 | B2 * | 10/2007 | Plopski | 208/46 |
| 7,309,435 | B2 | 12/2007 | Rozich | |

FOREIGN PATENT DOCUMENTS

| EP | 0 244 029 B1 | 11/1987 | | |
| EP | 0 193 999 B1 | 1/1988 | | |
| EP | 1344563 A2 * | 9/2003 | ............ | C08F 10/100 |
| EP | 1 181 252 B1 | 4/2004 | | |
| EP | 1595551 * | 11/2005 | ................ | A61L 2/04 |

OTHER PUBLICATIONS

Bouallagui et al., Bioreactor performance in anaerobic digestion of fruit and vegetable wastes, Process Biochemistry 40 (2005) 989-995.*
Wust, Single-phase and two phase cheese wastewater treatment by anaerobic SBRs, Thesis submitted to the Faculty of the Graduate School, Marquette Univeristy, May 2003, pp. 1-118.*
Blasig, et al., "Volatile fatty acid fermentation of AFEX-treated bagasse and newspaper by rumen microorganisms," Resources Conservation and Recycling, vol. 7, No. 1/03, Oct. 1, 1992, pp. 95-114, Elsevier Science Publishers B.V., Amsterdam, NL, XP000691007.
Xu, et al., "A comparative study of anaerobic digestion of food waste in a single pass, a leachate recycle and coupled solid/liquid reactors," Water Science and Technology, vol. 47, No. 1, 2003, pp. 319-324, XP-002547721.
Demirel, et al., "Two-phase anaerobic digestion processes: a review," Journal of Chemical Technology and Biotechnology, vol. 77, No. 7, pp. 743-745, Jul. 2002, XP-002547722.
Lepisto, et al., "Extreme Thermophilic (70° C.), VFA-Fed UASB Reactor: Performance, Temperature Response, Load Potential and Comparison with 35 and 55° C. UASB Reactors," Water Research, vol. 33, No. 14, pp. 3162-3170, Oct. 1, 1999, Elsevier, Amsterdam, NL, XP-004178722.
Wang, et al., "Effects of volatile fatty acid concentrations on methane yield and methanogenic bacteria," Biomass and Bioenergy, vol. 33, No. 5, Feb. 23, 2009, pp. 848-853, XP-026033716, Oxford, GB.
Search Report in International Application PCT/NL2010/050193 dated Jul. 23, 2010.

* cited by examiner

*Primary Examiner* — Suzanne M Noakes
*Assistant Examiner* — Stephen Chong
(74) *Attorney, Agent, or Firm* — Gilberto M. Villacorta; Sunit Talapatra; Foley & Lardner LLP

(57) ABSTRACT

The invention pertains to a process for producing methane by a two-stage anaerobic digestion of organic feed, comprising i) subjecting an organic feed suspension (a) to acidogenesis and methanogenesis in a first reactor (1); ii) withdrawing an effluent (b) from said first reactor and subjecting it to solid/liquid separation (2), thus obtaining effluents high (d) and low (c) in solids, wherein the volatile fatty acid (VFA) concentration in said first reactor is controlled by the withdrawal rate; iii) subjecting the effluent low in solids (c) to acidogenesis and methanogenesis in a second reactor (3), thus producing methane gas in said first and second reactor.

14 Claims, 2 Drawing Sheets

PROCESS FOR PRODUCING METHANE FROM BIOMASS

FIELD OF THE INVENTION

The invention pertains to an improved treatment of organic waste and/or biomass to more efficiently collect methane, focused on yield [liter $CH_4$ per kg of biomass] and kinetics [liter $CH_4$ per $m^3$ reactor per day]. The invention particularly relates to an improved two-phase procedure wherein conditions are provided to efficiently conduct methanogenesis in both phases, the conditions optimized for preventing accumulation of inhibiting products during the first phase.

BACKGROUND OF THE INVENTION

Considerable literature is available describing slurry reactors for industrial, municipal, agricultural and farm solid waste and/or biomass digestion. The biomass is mixed with water or effluent to at least partially suspend the solid particles for intimate contact with the microorganisms. To further increase suspension, mixing and contacting, a gas, such as biogas circulation, for example, may be added to the reactor vessel.

Outside the field of biomass conversion, the majority of anaerobic water treatments make use of the principle of "Upflow Anaerobic Sludge Blanket" (UASB), introduced in the 1970s and updated ever since. The principle is outlined in EP-A 193 999 and EP-A 244 029. The characteristic of the UASB reactor is that the water to be treated is fed in and distributed over the bottom of a tank, from where it flows slowly upwards through a blanket of bacterial biomass. The gas thus produced bubbles upwards and provides for a certain degree of mixing. As a result of clever positioning of gas collection hoods below the water surface, the gas bubbles do not reach the water surface, with the result that a calm zone is produced at the top and any sludge particles swirled up are able to settle into the blanket of bacterial biomass (the "sludge blanket") again.

In the art methane production from organic waste or biomass is often performed in two steps, acidogenesis and methanogenesis. In the acid digestion phase, volatile fatty acids (VFA), in particular acetic, propionic and butyric acid, are formed. In the scientific literature, a review is provided by Demirel Burak et al., Journal of Chemical Technology and Biotechnology, Vol. 77, No. 7, pp 743-755. In all processes, the acidogenic and methanogenic phases are kept physically separated. Some focus on VFA production, see e.g. Blasig J D et al., Resources, Conservation and Recycling, vol. 7, no. 1/03, pp 95-114. It teaches a continuous fermentation system with different removal rates for solids and liquids. As such, methanogenesis is considered disadvantageous and is avoided by manipulating fermentation conditions such as pH, temperature, and residence time.

Others attempt to improve the separate methanogenesis step: Xu H L et al., Water Science and Technology, Vol. 47, No. 1, 2003, pp 319-324, describe a coupled solid/liquid bioreactor, comprising a percolation reactor and an upward-flow anaerobic sludge blanket (UASB) reactor for the anaerobic digestion of food waste. Lepisto R et al., Water Research, Elsevier, Amsterdam, Vol. 33, No. 14, pp 3162-3170 focus on parameters influencing methanogenesis in UASB reactors. Wang Y et al., Biomass and Bioenergy, Vol. 33, No. 5, pp 848-853 also aim to control the volatile fatty acids concentrations in the methanogenic phase, in a single reactor concept.

The patent literature is no different. U.S. Pat. No. 4,022,665, EP 1,181,252 and U.S. Pat. No. 7,309,435 all describe methane production processes wherein the methane-forming fermentation phase is preceded by a separate acid digestion phase. The contents of these patent publications are hereby incorporated by reference.

In the art, these two-stage fermentors have been considered more effective than the conventional single-stage systems in the conversion of solid substrates to biogas. The reason rests in the fact that VFA production in concentrated feeds often proceeds at much faster rates than the subsequent conversion of VFA to methane, thereby causing acid accumulation and consequently inhibition of methanogenesis. A two-stage configuration was introduced to avert the imbalance between acidogenesis (i.e. VFA production) and methanogenesis by physically isolating these two major microbial phases in two separate bioreactors. VFA accumulation in the first reactor is often controlled by feeding—large—amounts of alkaline solution to said reactor. However, the use of additional streams of chemicals is often undesired. Also, both kinetic and thermodynamic biomass conversion rates are limited in these processes.

Hence, there is a continuous need in the art to improve the methanogenesis, in terms of yield [liter $CH_4$ per kg of biomass] and kinetics [liter $CH_4$ per $m^3$ reactor per day].

SUMMARY OF THE INVENTION

The inventors have recognized that control of VFA production and pH is of vital importance in biomass digestion or methane fermentation. However, this is where the overlap with the prior art ends, which points in the direction of physically separating acidogenesis and methanogenesis. Instead, the inventors have found that better methane production yields and rates are obtained when the contact time between the micro-organisms responsible for converting biomass into methane and the organic feed is optimized. To this end, biomass conversion into methane is performed in two subsequent stages of methanogenic conversion where the reactor configurations and conditions are adapted to the substrate concentrations and substrate qualities. A concentrated organic feed is fed to a first (slurry) reactor, where under methanogenic conditions VFA concentrations can build up, while inhibitory conditions are avoided by bringing (at least part of) the effluent of said first reactor—after an intermediate solid/liquid separation step—in a subsequent (preferably granular sludge) reactor. The second reactor is particularly adapted to convert the VFA into biogas at a fast rate and is thus able to avoid further VFA accumulation in the circuit. The second reactor type and conditions are selected such that the micro-organisms responsible for converting biomass into methane are much more close together in the second reactor. In a preferred embodiment, the second reactor is a so called granular sludge reactor. At least part of the VFA-depleted second reactor effluent can be returned to the first reactor. By conducting the conversion of biomass in methane [and $CO_2$] in these two distinct reactor types, the inventors have connected the—thus far unrelated—fields of biomass conversion and (waste) water treatment.

The process diverges from the two-stage processes for converting biomass known in the art, which rely on separate hydrolytic/acidogenic and methanogenic phases, such as disclosed in EP 1,181,252 and Demirel Burak et al., Journal of Chemical Technology and Biotechnology, Vol. 77, No. 7, pp 743-755. The present process is characterized by both reactors containing the same or similar mixed acidogenic and methanogenic population, but relying on distinctly different reactor concepts.

In the process according to the invention, the microbial population in the first reactor is safeguarded by controlling the rate of withdrawal of effluent from the first reactor, and therewith withdrawal of VFA, to subsequent processing steps, focusing on the VFA accumulation in the reactor. In practice, VFA levels in the first, preferably slurry, reactor are preferably maintained below 4 g per liter, more preferably below 3 g per liter, most preferably below 2 g per liter. Since reliable monitoring of VFA content is sometimes found difficult, and pH in the system is at a certain level related to the VFA content, pH measurements can be used as an on-line steering parameter. VFA concentrations can also be controlled on a regular basis by applying analytical measurements. In one embodiment, it is preferred to maintain the pH in the first reactor at a value higher than 5.5, more preferably at least 6, most preferably at least 6.5; if the suspension tends to acidify, the rate at which effluent is withdrawn from the first reactor is increased, to avoid VFA accumulation. In one embodiment, VFA concentration and/or pH may be monitored inline and/or continuously.

After treating the effluent by solid/liquid separation, the concentrated stream containing (partly) unfermented organic feed is separated off, and the unconcentrated, liquid stream containing (partly) unfermented insoluble materials, but mostly soluble organics and VFA, is fed to the subsequent second reactor. There, the unconcentrated stream is subjected to acidogenesis and methanogenesis. VFA are converted into carbon dioxide and methane. Its format permits a more efficient reduction of VFA into methane and carbon dioxide while simultaneously requiring reduced reactor volumes. Part of the liquid of the second reactor with reduced VFA content can readily be returned to the first reactor, thus providing excellent means to control VFA accumulation in the first reactor. For sake of completeness it is noted that there is less need for VFA control in (the effluent of) the second reactor.

The present setup allows for semi-continuous or continuous biogas production from organic feed.

LIST OF FIGURES

Figure 1:
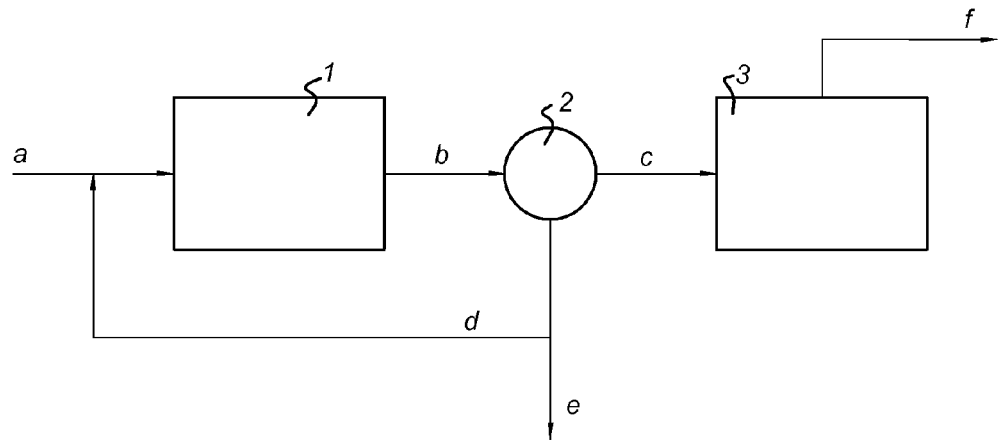
FIG. 1 is a schematic representation of a two stage methanogenesis process, comprising a slurry reactor (1) and a granular sludge reactor (3), separated into streams high and low in solids in separation means/unit (2)
Figure 2:
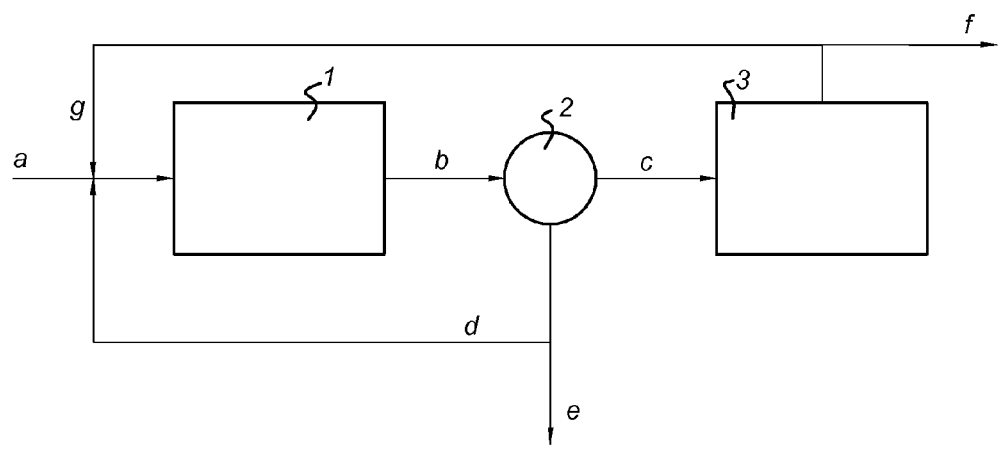
FIG. 2 is the two-stage methanogenesis process shown in FIG. 1, wherein a part of the effluent of the second reactor is recirculated to the first reactor.
Figure 3:
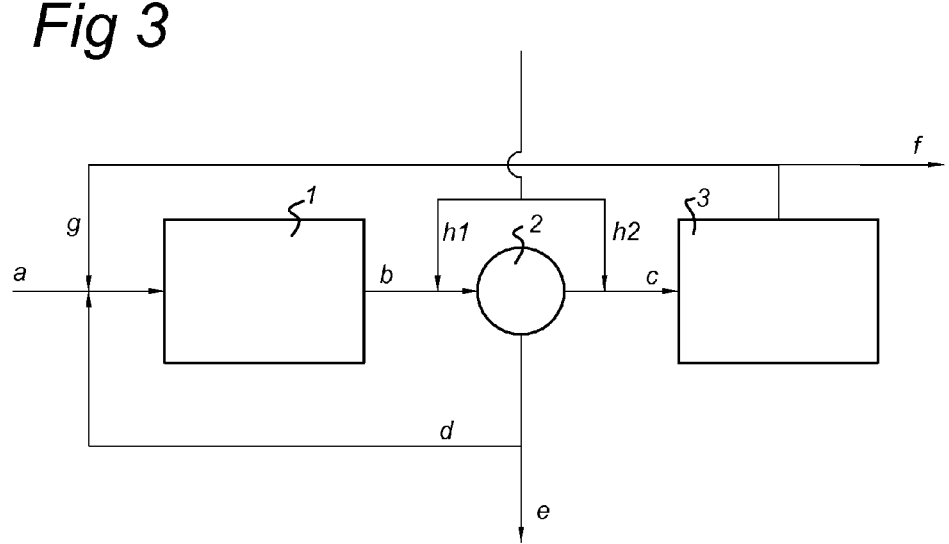
Figure 4:
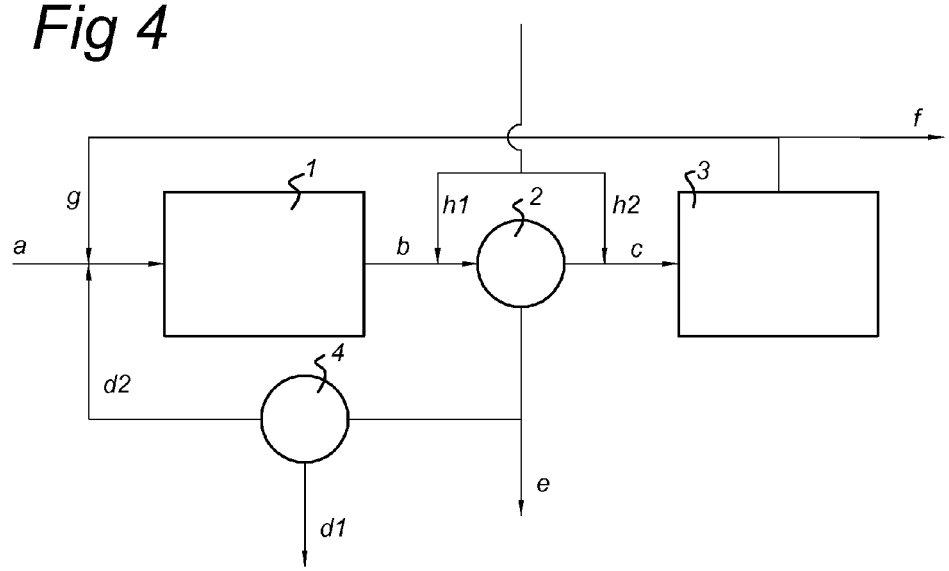

FIG. 3 shows the methanogenesis process of FIGS. 1 and 2, wherein a stream comprising mainly soluble organic materials is added to the effluent (b) either before or after solid/liquid separation, dependent on its content of suspended solids; and FIG. 4 shows additional processing means (4) for treating (part of) the effluent high in solids (d) before returning (part of) it to the slurry reactor (1).

DETAILED DESCRIPTION OF THE INVENTION

In the following, the two-stage methanogenesis of the present invention will be discussed in terms of the elements shown in the FIGS. 1-4. The figures are merely illustrative and do not limit the teaching of the invention. Modifications or changes therein without departing the scope of the invention are considered to fall within the ambit of the skilled person's knowledge.

The invention pertains to a process for producing methane by a two-stage anaerobic digestion of organic feed, comprising:
i) subjecting an organic feed suspension (a) to acidogenesis and methanogenesis in a first reactor (1);
ii) withdrawing an effluent (b) from said first reactor and subjecting it to solid/liquid separation (2), thus obtaining effluents high (d) and low (c) in solids, wherein the volatile fatty acid (VFA) concentration in said first reactor is controlled by the withdrawal rate;
iii) subjecting the effluent low in solids (c) to acidogenesis and methanogenesis in a second reactor (3);
thus producing methane gas in said first and second reactor. The VFA levels are controlled in step (ii) to levels below inhibitory to methanogenesis.

To complete the process as depicted in FIG. 1, where separating at stage (2), a stream (e) comprising effluent high in solids may be discharged from the circuit. Also depicted is a stream (f) released from the second reactor, comprising liquid effluent low in organics and VFA, but high in inorganic nutrients such as ammonia, phosphate etc. Not shown, biogas produced in reactors (1) and (2) is extracted, transported and collected using conventional methods.

In a preferred embodiment (FIG. 2) at least part of the second reactor effluent (g) is returned to said first reactor. Hence, the volatile fatty acid (VFA) concentration in said first reactor is controlled by the withdrawal rate of effluent (b) and the return of at least part, preferably a predominant part, more preferably all of the second reactor effluent (g) to said first reactor. Due to the efficient VFA conversion in the second reactor, the VFA concentration in the second reactor effluent (g) is lower than that of the first reactor effluent (b), preferably by at least a factor 10, more preferably at least a factor 15, most preferably at least a factor 20. By recirculating (part of) the VFA-poor stream (g), it prevents VFA accumulation in the first reactor, thus allowing further methanogenesis.

In another preferred embodiment (FIG. 3) a stream comprising (mainly) soluble organic cell matter is added before (h1) and/or after (h2) solid/liquid separation (2). Preferably, the stream is obtained from the organic waste and/or biomass prior to the digestion process, preferably by leakage and/or mechanical treatment, and/or originates from dewatering biomass. It may depend on the concentration of suspended solids in the stream whether it is fed before (h1) or after (h2) solid/liquid separation. It advantageously adds valuable rest materials to the process which would otherwise have been discarded, or in the present most sustainable way by adding in the first reactor, have a negative effect on the residence time in the first reactor.

In yet another preferred embodiment (FIG. 1-4) at least part of the effluent high in solids (d) is returned to the first reactor, maintaining the concentration of (partly) unfermented organic material in the first reactor.

In yet another preferred embodiment (FIG. 4) at least part of said effluent high in solids (d) is processed in a processing means (4) before return to said first reactor (1). The further processing step may involve some physical, chemical, thermal, enzymatic and/or mechanical action. An example is an additional step to remove or process fibres present in the organic feed stream. These may thus be removed from the anaerobic digestion circuit, either to concentrate the organic feed further, or to use such valuable materials elsewhere. Such a step may also be incorporated at another stage of the process, but stream (d) has a beneficially high concentration of solids, rendering it more efficient to apply additional processing steps there. The optional addition step subdivides 'unprocessed' stream (d) in a stream (d2) that is returned to the first reactor, and a stream (d1) that is discharged from the process.

In one embodiment, the pH in the first reactor is preferably 7.5 or less, more preferably 7.2 or less. This is conveniently lower than the pH levels between 7.5 and 8.3 usually maintained in the fermentors known in the art. Consequently, the fermentation in the second reactor downstream is also operated at lower pH levels, advantageously preventing precipitation issues.

Most preferably, the above preferred embodiments are combined altogether.

The "anaerobic digestion" treatment involves biological decomposition or fermentation of organic and inorganic matter in which the micro-organisms are indifferent to the presence or absence of oxygen; it involves a first, acid-forming or "acidogenic" process in which large organic molecules are broken down and partially oxidized to form lower molecular weight organic acids, and a second, methane-forming or "methanogenic" process in which the lower molecular weight organic acids are converted into gaseous carbon compounds, primarily methane (and carbon dioxide). In the two-stage anaerobic digestion process of the present invention acidogenesis and methanogenesis are performed simultaneously, in the same reactor environment. In other words, both reactors comprise acidogens and methanogens.

Organic Feed

With the term "organic feed" both biomass and organic waste is meant. Biomass comprises fibrous plant matter originating from dedicated energy crops and trees, agricultural crops, as well as agricultural crop wastes and residues, wood wastes and residues, while with organic waste, municipal wastes, manure, animal waste, landfill gas and other waste materials are designated. It preferably excludes organic material which has been transformed by geological processes into substances such as coal or petroleum.

Organic feeds that are particularly suited for the present invention comprise agricultural food and feed crops, agricultural crop residues, and by-products from the agricultural crops processing industry. Preferably, the organic feed comprises sugar beets and/or leaves and all (by-) products from sugar beet processing industry.

Micro-Organisms

It is not an aim of the inventors to change the microbial population conventionally applied in anaerobic digestion processes.

There are several types of bacteria that are involved in the process of anaerobic organics digestion including acidogens, which convert the monomers resulting from hydrolysis of the organic feed into VFA; acetogens converting VFA into acetic acid, carbon dioxide, and hydrogen; and methanogens converting acetates into methane and carbon dioxide, while consuming hydrogen. These bacterial communities feed upon the initial feedstock, which undergoes a number of different processes converting it to intermediate molecules including sugars, hydrogen and acetic acid before finally being converted to biogas. Different species of bacteria are able to survive at different temperature ranges. The reactor conditions are adapted to these conditions, preferably in the range of 30 and 70° C.

Suitable bacteria are those living optimally at temperatures between 35-40° C. and called mesophiles or mesophilic bacteria. Some of the bacteria can survive at the hotter and more hostile conditions of 55-60° C., these are called thermophiles or thermophilic bacteria. Suitable bacteria are for instance disclosed in the citations provided in the background section, their content herewith incorporated by reference.

Although it is possible to apply different sets of acidogens, acetogens and/or methanogens in reactors (1) and (3), it is preferred that reactors (1) and (3) comprise similar or identical microbial populations. Differences in concentrations may well relate to the organic feed supply and retention times. The concentration of organic matter can be expressed in terms of Volatile Total Solids in the reactor content (gram VTS per liter). In the first reactor the concentration is preferably in the range between 20 and 100 g/l, more preferably about 50 g/l, and the amount of bacteria (active biomass) is preferably calculated at approximately 30-50% of the VTS content. The concentration of organic matter in the second reactor is preferably in the range between 40 and 140 g/l, more preferably 40-120 g/l, more preferably about 80 g/l, where the amount of bacteria (active biomass) is preferably calculated at approximately 40-80% of the VTS content.

First Reactor

In a preferred embodiment of the invention, the first reactor is a slurry reactor. Slurry reactors are commonly used for the biological, chemical or enzymatic conversion of soluble and insoluble reactants. In the context of the invention, the organic feed (a) is preferably standardized to 5-30 wt %, preferably 10-20 wt % of organic matter—not including micro-organisms—suspended in water. Slurry concentrations (including micro-organisms) in the first reactor are typically between 4-40 wt %, preferably between 5-15 wt %.

The slurry reactor has means to effectuate and maintain a suspension of particles in a liquid. If deemed necessary, it may involve agitation, e.g. mixing, or gas supply to further promote suspension and/or contact between micro-organisms and organic feed.

Typical treatment capacities of the slurry reactor are 3-10 kg, preferably 3-7 COD/m$^3$ per day; "COD" (chemical oxygen demand) is an expression of the amount of oxygen that is theoretically necessary to convert organic compounds to carbon dioxide.

The hydraulic residence time is at least 10 days, preferably of the order of 20-60 days. The organic loading rate is preferably about 3-8 gram, preferably 3-6 gram of organics per liter reactor content per day.

A typical example of a bioslurry or slurry reactor suitable for carrying out the invention is a cylinder-type reactor. In the art, suitable examples are given in U.S. Pat. No. 5,057,284 and U.S. Pat. No. 5,616,304, their contents herein incorporated by reference. Such reactors are vessels containing a slurry, i.e. mixture of a liquid and solid particles, wherein at least a portion of the solid particles are suspended in the liquid. When the reactor vessel contains microorganisms and a slurry, it is generally referred to as a bioslurry reactor. Slurry or bioslurry reactors may be mechanically stirred, e.g. using turbine mixers, or unstirred. If they are unstirred, mixing may occur as gas bubbles generated in said vessel rise through the slurry. In a preferred embodiment of the invention, no mechanical stirring is present.

Second Reactor

In a preferred embodiment of the invention, the second reactor is a granular sludge reactor, comprising sludge granules. The underlying mechanism is described in the background section. Sludge granules are at the core of granular sludge reactor concepts. A sludge granule is an aggregate of micro-organisms forming during biomass conversion in an environment with a constant upflow hydraulic regime. In the absence of any support matrix, the flow conditions create a selective environment in which only those micro-organisms capable of attaching to each other survive and proliferate.

Eventually the aggregates form into dense compact biofilms referred to as "granules". Due to their large particle size, generally ranging from 0.5 to 10 mm in diameter, more preferably 1-5 mm, most preferably about 1-3 mm, the granules resist washout from the reactor, thus permitting high hydraulic loads. Additionally, the biofilms are compact, allowing for high concentrations of active micro-organisms and thus high organic space loadings in granular sludge reactors. The dense populations of micro-organisms promote the conversion rate.

Typical treatment capacity of the sludge reactor is 15-40, preferably 20-35 kg COD/m$^3$ per day. The hydraulic residence time is of the order of hours, preferably 1-20 hours, more preferably 4-10 hours.

Sludge concentrations in the second reactor are typically between 40 and 120 g/l as organic matter. The denser concentrations of micro-organisms in this reactor allow much higher organic loading rates, preferably 25-30 gram of organics per liter reactor content per day. In one suitable type of granular sludge reactor, the liquid feed is passed upwards through an anaerobic granular sludge bed where substrates in the liquid feed come into contact with the micro-organisms in the sludge. The upward motion of released gas bubbles causes hydraulic turbulence that provides reactor mixing without any mechanical parts. At the top of the reactor, the water phase is separated from sludge solids and gas in a three-phase separator (also known the gas-liquid-solids separator). This concept is known in the art as the upward-flow anaerobic sludge blanket (UASB) reactor.

Also suitable is the expanded granular sludge bed reactor with external circulation (EGSB) or with internal circulation (IC). In essence the working mechanism is similar. The distinguishing feature is that a faster rate of upward-flow velocity is designed for the liquid feed passing through the sludge bed. The increased flux permits partial expansion (fluidization) of the granular sludge bed, improving feed-granule contact as well as enhancing segregation of small inactive suspended particle from the sludge bed.

In a preferred embodiment of the invention, a granular sludge reactor with internal circulation is employed.

Solid/Liquid Separation

Since the second reactor is water-driven, as many solids as possible need to be removed from the effluent of the slurry reactor prior to entering the second reactor. It is preferred that the suspended solids content of the feed to the second reactor (c) is lower than 5 g per liter, more preferable lower than 2 gram per liter. This is achieved by solid/liquid separation, for instance using membrane or centrifugal separation and/or gravity.

The effluent leaving S/L separation may involve concentration steps, such as comprising high pressure, high temperature and/or enzymatic treatment.

VFA Concentration, pH

Because of the combined acidogenesis and methanogenesis in single reactor environments, it is essential to prevent build-up of VFA which could otherwise intoxicate and kill off the methanogens present in the reactor. As explained before, the special conditions in the second reactor, such as formation of granular sludge, enable methanogenesis to proceed at much faster rates than VFA production, thus providing a tool to repress the VFA concentration in the circuit. The second reactor simply cleans the VFA-rich effluent originating from the first reactor and returns a VFA-poor stream to the first reactor. Consequently, the first reactor is maintained in its methanogenic state, i.e. continues to convert VFA to biogas, resulting in a pH that remains non-acidic, i.e. preferably not below pH 5.5.

It is preferred that the total concentration of VFA in the liquid phase in the first reactor does not exceed 4 g/l, more preferably does not exceed 3 g/l, most preferably does not exceed 2 g/l. It is particularly preferred to maintain the propionic acid concentration in the effluent of the first reactor below 600 mg/l, preferably below 200 mg/l.

It is preferred that the total concentration of VFA in the effluent of the second reactor does not exceed 400 mg/l, more preferably not exceed 100 mg/l. It is especially preferred that the numbers on VFA concentration in this paragraph apply to the (relative) amounts of acetic, propionic and butyric acid. It is particularly preferred to maintain the propionic acid concentration in the effluent of the second reactor below 100 mg/l.

Control of the VFA concentration is achieved by the additional treatment of the liquid part of the first reactor effluent (FIG. 2, stream (c)) in the second reactor, and by circulating part of the second reactor effluent to the first reactor (FIG. 2, stream (g)). Unlike the prior art, the invention does not encompass means to control pH by providing chemicals (alkaline salts) to the reactor. In essence, the anaerobic digestion involves no other input than organic feed and (preferably at the start) conventional anaerobic micro-organisms to ferment said feed.

VFA concentration can be determined by applying gas chromatography, High Performance Liquid Chromatography or semi-quantitative analyses such as titrimetric or photometric measurements. Alternatively, pH measurements can be used as steering parameter, preferably continuously and/or in-line, as described for example in EP 1,181,252, its contents herein incorporated by reference Biomass Leak Water/Juice Since the reactor set-up according to the invention makes it possible to operate in separate largely solid (first reactor) and more liquid (second reactor) phases, it is possible to independently add additional solid and liquid feeds to the respective phases of the system.

In a preferred embodiment according to the invention, additional material, preferably mainly soluble organic cell material, not originating from the first reactor, is fed to the second reactor. This is indicated as streams h1 and h2 in FIG. 3, where the stream (h2) is either directly fed—as a liquid stream—to the second reactor, or first subjected to solid/liquid separation (h1) prior to entering the second reactor. In the latter case, the stream h1 may contain high concentrations of suspended solids, preferably more than 5 gram per liter, more preferable more than 2 gram per liter. In the other case, stream (h2) may contain high concentrations of soluble organics, but low in suspended solids, preferably lower than 5 gram per liter, more preferably lower than 2 gram per liter subsequent treatment in the second reactor.

Preferably, the stream(s) (h1) and/or (h2) comprises leakage moisture or juice, preferably the juice of beet leaf, that would otherwise leak into the ground when beet leaves are left on the field, or leak out when stored elsewhere. The present invention makes it possible to store agricultural crops and residues all year round, treat the solid material in the first reactor while directly introducing the leak moisture via streams h1 and/or h2 to the system.

Another example of a stream that may be added to the biogas production process of the invention is the juice/moisture that is derived from dewatering biomass.

The invention also pertains to a methane production or biomass digestion or methane fermentation installation/unit comprising a first reactor (1) and a second reactor (3) subsequently arranged, wherein said first reactor comprises an outlet that is connected via a solid/liquid separation unit (2) to the inlet of the second reactor, wherein said separation unit has means to forward a stream relatively low in solids (c) to said second reactor, and means to return a stream relatively high in solids (d) to said first reactor, and wherein said second reactor optionally comprises an outlet that can return part of the VFA-poor organic feed effluent (g) to said first reactor, and wherein said reactors both comprise acidogens and methanogens to anaerobically ferment organic feed subjected to said first reactor (a) into methane. It is preferred that the first reactor is a slurry or bioslurry reactor; it is preferred that the second reactor is a granular sludge reactor. It is preferred that the first reactor and/or effluent (b) comprises means (e.g. sensors, pH indicators etc.) for monitoring and/or controlling VFA concentration. The term 'VFA-poor' reflects the relatively high methanogenesis rate in the second reactor, thus reducing the relatively high concentration of VFA withdrawn from the first reactor to a lower level.

The installation may further comprise means (4) to mechanically, chemically, physically, enzymatically or thermally process stream (d). The installation may be used to perform the process as detailed above. The details presented there equally apply here.

The invention also relates a plant comprising such an installation.

The invention claimed is:

1. A process for producing methane by a two-stage anaerobic digestion of organic feed, comprising:
   (a) subjecting an organic feed suspension to acidogenesis and methanogenesis in a slurry reactor;
   (b) subjecting a first effluent from the slurry reactor to solid/liquid separation, thus obtaining effluents high and low in solids;
   (c) subjecting the effluent low in solids to acidogenesis and methanogenesis in a granular sludge reactor,
   wherein at least part of a second effluent stream is withdrawn from the granular sludge reactor and returned to the slurry reactor,
   wherein volatile fatty acid (VFA) concentration in the slurry reactor is controlled by the withdrawal rate of the first effluent stream and the return rate of the second effluent stream to the slurry reactor; and
   wherein acidogenesis and methanogenesis are performed simultaneously in both reactors to produce methane gas in both reactors.

2. The process according to claim 1, wherein at least part of the effluent high in solids is returned to the slurry reactor.

3. The process according to claim 1, wherein the VFA concentration in the slurry reactor is controlled at a level lower than 4 g/liter and/or the pH in the slurry reactor is maintained at a value higher than 5.5.

4. The process according to claim 1, wherein the VFA concentration in the second effluent stream is at least a factor 10 lower than that in the first effluent stream.

5. The process according to claim 1, wherein the organic solids content in the slurry reactor is in the range of 2-10 wt %, and wherein the organic solids content in the granular sludge reactor is between 40 and 120 g/liter.

6. The process according to claim 1, wherein the slurry reactor has a loading capacity of 3-10 kg COD/$m^3$/day, and the granular sludge reactor has a loading capacity of 15-40 kg COD/$m^3$ per day.

7. The process according to claim 1, wherein the slurry reactor has a hydraulic residence time of at least 10 days, and the granular sludge reactor has a hydraulic residence time of 1-20 hours.

8. The process according to claim 1, further comprising adding a stream comprising soluble organic cell material.

9. The process according to claim 8, wherein the soluble organic cell material is obtained from leakage, mechanical treatment, dewatering biomass, and/or leak moisture of organic waste and/or biomass.

10. The process according to claim 9, wherein the soluble organic cell material is obtained from beet and beet leaf leak moisture and juice.

11. The process according to claim 1, wherein the organic feed comprises agricultural crops, agricultural crop residues, and/or by-products from agricultural crops processing.

12. The process according to claim 11, wherein the organic feed comprises sugar beet and/or leaves.

13. The process according to claim 1, wherein the slurry reactor comprises both acidogens and methanogens, and wherein the granular sludge reactor comprises both acidogens and methanogens.

14. The process according to claim 1, wherein the slurry reactor and the granular sludge reactor comprise substantially the same population of acidogens and methanogens.

* * * * *